(12) United States Patent
Griffith

(10) Patent No.: US 7,623,929 B1
(45) Date of Patent: Nov. 24, 2009

(54) CURRENT SENSING COIL FOR COCHLEAR IMPLANT DATA DETECTION

(75) Inventor: Glen A Griffith, Newbury Park, CA (US)

(73) Assignee: Advanced Bionics, LLC, Valencia, CA (US)

( * ) Notice: Subject to any disclaimer, the term of this patent is extended or adjusted under 35 U.S.C. 154(b) by 537 days.

(21) Appl. No.: 10/651,650

(22) Filed: Aug. 29, 2003

Related U.S. Application Data

(60) Provisional application No. 60/407,262, filed on Aug. 30, 2002.

(51) Int. Cl.
    *A61N 1/08* (2006.01)
(52) U.S. Cl. .......................................... 607/57; 607/60
(58) Field of Classification Search .............. 607/55–57, 607/65, 59–61
    See application file for complete search history.

(56) References Cited

U.S. PATENT DOCUMENTS

| | | | |
|---|---|---|---|
| 3,218,638 A | 11/1965 | Honig | |
| 3,867,950 A * | 2/1975 | Fischell | 607/33 |
| 4,160,971 A * | 7/1979 | Jones et al. | 340/870.26 |
| 4,495,384 A | 1/1985 | Scott et al. | |
| 4,532,930 A * | 8/1985 | Crosby et al. | 607/57 |
| 4,654,880 A * | 3/1987 | Sontag | 455/41.2 |
| 4,918,745 A | 4/1990 | Hutchison | |
| 5,069,210 A * | 12/1991 | Jeutter et al. | 607/57 |
| 5,179,511 A | 1/1993 | Troyk et al. | |
| 5,569,307 A | 10/1996 | Schulman et al. | |
| 5,603,726 A | 2/1997 | Schulman et al. | |
| 5,626,629 A | 5/1997 | Faltys et al. | |
| 5,741,314 A | 4/1998 | Daly et al. | |
| 5,758,651 A | 6/1998 | Nygard et al. | |
| 6,134,474 A * | 10/2000 | Fischell et al. | 607/45 |
| 6,185,452 B1 * | 2/2001 | Schulman et al. | 604/20 |
| 6,205,360 B1 | 3/2001 | Carter et al. | |
| 6,301,505 B1 | 10/2001 | Money | |
| 6,321,118 B1 | 11/2001 | Hahn | |
| 6,496,734 B1 | 12/2002 | Money | |
| 6,510,345 B1 * | 1/2003 | Van Bentem | 607/60 |
| 6,603,858 B1 | 8/2003 | Raicevich et al. | |
| 2003/0012390 A1 | 1/2003 | Franks | |
| 2003/0135247 A1 | 7/2003 | Zierhofer | |
| 2003/0171787 A1 | 9/2003 | Money et al. | |

FOREIGN PATENT DOCUMENTS

WO    WO-02/089913 A2    11/2002

* cited by examiner

*Primary Examiner*—Mark W Bockelman
*Assistant Examiner*—Eric D Bertram
(74) *Attorney, Agent, or Firm*—Wong, Cabello, Lutsch, Rutherford & Brucculeri LLP

(57) ABSTRACT

A detection circuit for sensing signals in an implantable cochlear stimulator is provided. The detection circuit has a primary coil winding which is part of the detected circuit. The primary coil is placed adjacent to and coupled electromagnetically to a secondary coil winding which is connected to an isolated circuit. The isolated circuit has circuit means for processing the induced current in the isolated current. Because a transformer is employed, the detection circuit draws only minimal power from the detected circuit, and the sensed output voltage can be flexibly scaled.

14 Claims, 5 Drawing Sheets

TEST WAVEFORMS  UPPER TRACE: V1 INPUT VOLTAGE  LOWER TRACE: DETECTED OUTPUT VOLTAGE

CURRENT SENSING COIL FOR COCHLEAR IMPLANT DATA DETECTION

The present application claims the benefit of U.S. Provisional Application Ser. No. 60/407,262, filed 30 Aug. 2002, which application is herein incorporated by reference in its entirety.

FIELD OF THE INVENTION

The present invention relates to current sensing methods and devices and, more particularly, those detection methods and devices for use with a cochlear implant device.

BACKGROUND OF THE INVENTION

Medical science has made great strides in enabling the profoundly deaf to hear. Such individuals can now hear with the aid of a specialized neural stimulation device referred to as a "cochlear stimulator."

An example of an implantable cochlear device that implements the above process has two main components: (a) a wearable or external system and (b) an implantable system. The external (wearable) system can include a speech processor coupled to a headpiece. The speech processor can include a battery or equivalent power source and further include electronic circuitry such as a microprocessor that converts sound waves to electrical signals and processes these signals in accordance with a desired speech processing strategy. The headpiece, which can be adapted to be worn by a patient behind the ear, can include a microphone for capturing ambient sound waves and converting them into electrical signals and, further, include an antenna or coil for transmitting the processed signals through the skin to the implantable system.

The implantable system, referred to hereinafter as an "implantable cochlear stimulator" ("ICS"), contains no power source, but instead receives its operating power from the external system which contains the battery. The ICS outputs a multiplicity of current stimulation channels, each channel connected to at least one electrode contact within the cochlea. Typically, however, each stimulation channel is uniquely connected to only one stimulating electrode, although the return connection of one channel may be connected uniquely to one return electrode contact or, alternatively, more than one return connection may be connected to a common, indifferent electrode such as the case of the ICS. Electronic circuitry can also be included in the ICS that permits the sign (polarity) and magnitude of the output current of each of the stimulation channels to be programmably specified at short-duration, predetermined intervals. An example of an implantable system which receives power from an external power source is provided in U.S. Pat. No. 5,603,726 which is incorporated herein by reference.

In operation, the microphone converts ambient sound waves into electrical signals which are processed by the signal processor. The processed signals are passed transcutaneously via a pair of electromagnetically coupled transmitter/receiver coils. The signals are further processed and transformed within the implantable system to generate complex stimulation waveforms at the times and durations specified and these waveforms are passed to the intra-cochlear electrodes which deliver electrical stimulation currents to the auditory nerves. As a result, the individual perceives an auditory sensation.

Detection of the speech processor data signals within the ICS electronic circuitry is necessary for a number of functions. A conventional data detection function in cochlear implant devices is performed by measuring the average voltage developed across a current sensing resistor which is placed in the RF power rectification circuit. This detection circuit provides a signal having good fidelity, but disadvantageously, can also reduce the voltage and power available to the stimulation channels, since the detection circuit is directly inserted within the rectifier. Conserving device power is critically important in a battery-powered, implantable, cochlear stimulation system, since it is inconvenient for the user to frequently recharge or replace batteries. Furthermore, a rechargeable battery can only be recharged a finite number of times before useful end of life is reached. As such, frequent battery recharging hastens the end of useful life, at which point, the battery must be discarded.

Conserving battery power is even more important with advanced cochlear implant devices capable of processing complex, multi-channel signals because such devices consume battery power more quickly than older systems having fewer channels and simpler processing. In addition, a two-part cochlear implant system, comprised of an external processing unit and an implantable unit, commonly employs a pair of transmitter/receiver coils which are electromagnetically coupled. Such a coupling can be relatively inefficient and can dissipate a substantial amount of power. It is important, therefore, that every circuit in the device, including any detection circuit, be optimized for the most efficient operation.

A conventional data detection circuit presents another disadvantage in that the signal voltages developed are below the lowest voltage available in the cochlear implant and, consequently, the weak signals obtained may be difficult to process. It would be desirable to have a detection system which can provide stronger voltage signals for easier processing, yet do so efficiently.

Thus, there is a need for a data detection circuit to be used in a cochlear implant device that conserves available battery power, while providing detected signal voltages which can be easily processed.

SUMMARY OF THE INVENTION

The present invention addresses the above and other needs by overcoming the disadvantages enumerated above.

In one aspect of the invention, a detection circuit is provided for sensing current signals in an ICS circuit comprising: a primary coil winding in the ICS circuit; a secondary coil winding placed adjacent to the primary coil winding, the secondary coil connected to an isolated part of the detection circuit; and means for processing induced current in the isolated part of the detection circuit. The means for processing the induced current can be an isolated detection circuit comprising: a diode connected in series with the secondary coil winding, a capacitor connected in series with the diode, and a resistor connected in parallel with the capacitor and in series with the diode.

In another aspect of the invention, a method is provided for detecting a current signal in an ICS circuit comprising: providing a primary coil winding in the ICS circuit; providing a secondary coil winding placed adjacent to the primary coil winding, the secondary coil a part of an isolated circuit; and sensing the induced current flow through the secondary coil winding.

It is a feature of the present invention to provide an electrical detection circuit which does not significantly reduce the power available to the power supply feeding the stimulation circuit.

It is another feature of the invention to provide an electrical detection circuit wherein the detected signal voltage is of sufficient strength so as to be easily processed.

It is yet another feature of the present invention to provide variable scaling of the detected signal to provide flexible signal processing capability.

BRIEF DESCRIPTION OF THE DRAWINGS

The above and other aspects, features and advantages of the present invention will be more apparent from the following more particular description thereof, presented in conjunction with the following drawings wherein.

Corresponding reference characters indicate corresponding components throughout the several views of the drawings.

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

The present invention provides a detection circuit that can sense current in an ICS rectifying circuit by employing an isolated voltage reference. Because a transformer is used to sense current in the ICS rectifying circuit, the detection circuit draws less power from the rectifying circuit compared to the presently practiced detection circuit which introduces an additional resistor into the ICS rectifying circuit. The use of the transformer also reduces the impedance of the rectifying circuit which permits greater flexibility in controlling the detector's rise and fall times.

Figure 1A:
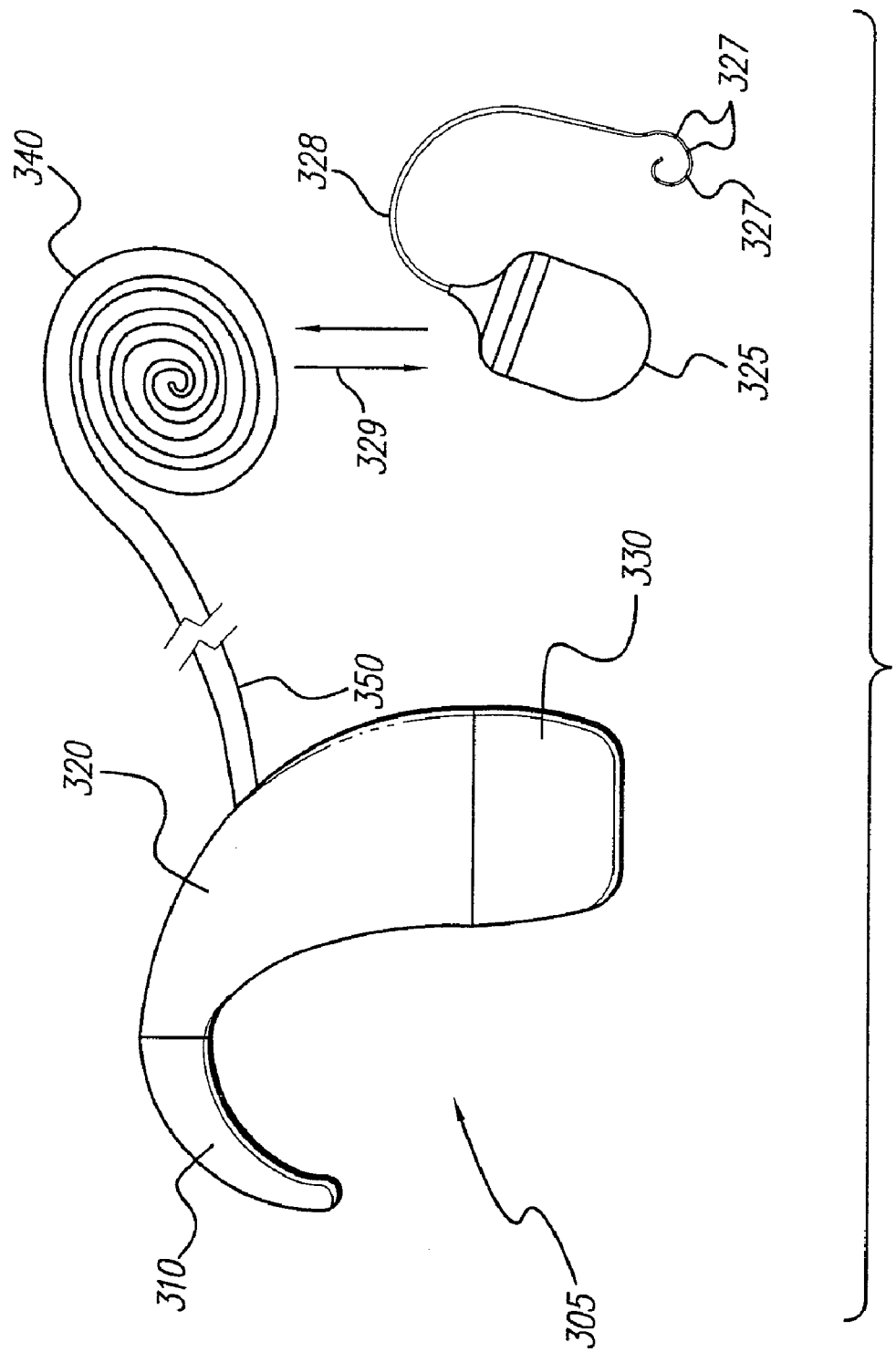
FIG. 1A shows an illustration of a conventional cochlear stimulation system that is partially implantable.

FIG. 1A shows an illustration of a conventional cochlear stimulation system. The complete cochlear stimulation system consists of a behind-the-ear device (BTE) 305, a transmitting coil/antenna 340, an implantable cochlear stimulating system 325 (ICS) and stimulating lead 328 with electrode contacts 327.

The particular embodiment of the BTE 305 has three separable pieces, an earhook 310, a main body 320 and a battery portion 330. The earhook 310 is detachable from the main body 320. Similarly, the battery portion 330 is also detachable from the main body 320. The battery contained in the battery portion 330 may be a rechargeable battery or it may be a primary, one-time-use-only, disposable battery. The BTE unit 305 is electrically coupled via an insulated, conductor 350 to a power transmitting coil/antenna 340 (headpiece). The housing of ICS 325 contains an implanted receiving coil (shown as L1 in FIG. 1B). A cochlear stimulating lead 328 can be connected to the ICS 325 which lead has a multiplicity of electrode contacts 327 that are used to stimulate the ganglion nerves inside the patient's cochlea.

The transmitting coil 340 can be placed over an implantable portion of the cochlear stimulator (ICS) 325 which contains the implanted receiving coil. The ICS implanted receiving coil can accept data signals and RF power from the power transmitting coil 340 as well as send back signals via the transmitting coil as signified by the arrows 329. The transferred RF power in the ICS 325 can be rectified and used to drive a multiplicity of stimulation channels to deliver stimuli through the electrode contacts 327.

Figure 1B:
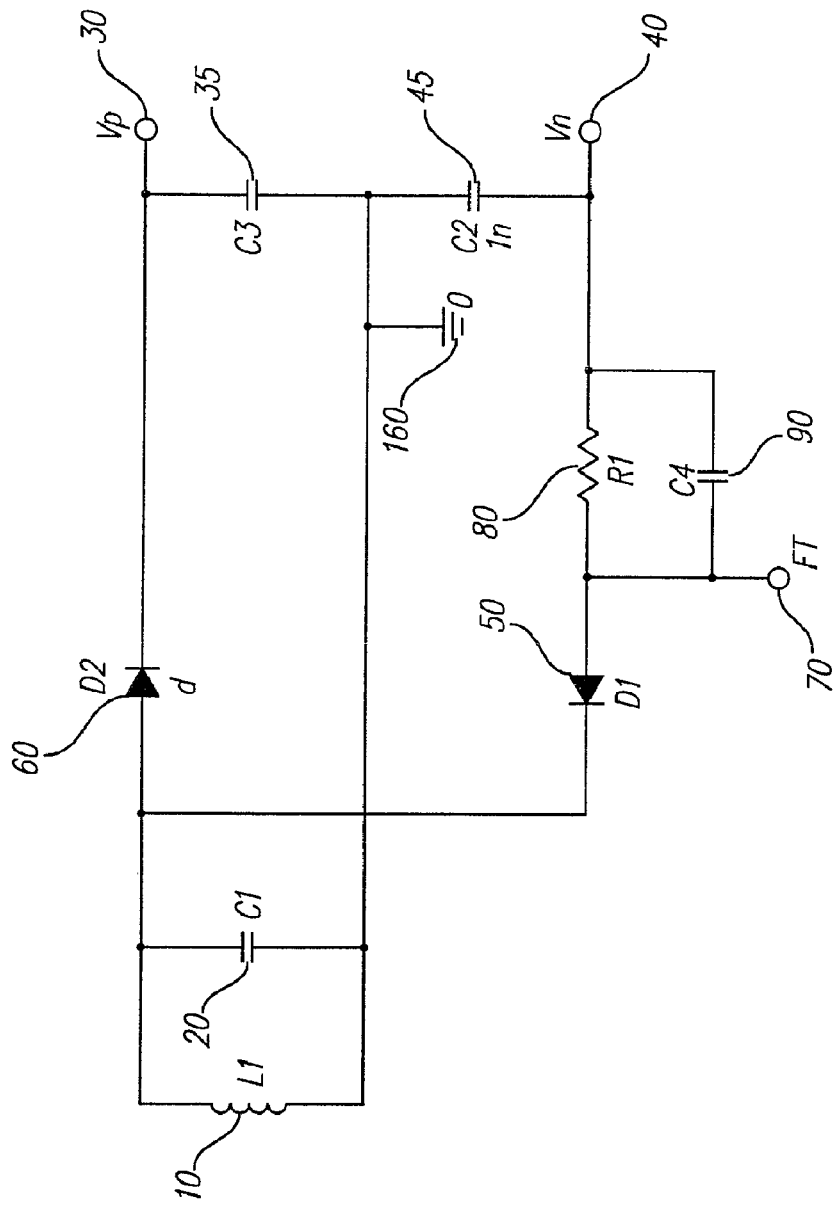
FIG. 1B shows a schematic diagram of a presently used sensing detection circuit incorporated into a rectification circuit which is part of an ICS.

FIG. 1B is a schematic circuit diagram showing a conventionally practiced rectifying and detection circuit contained within an implantable cochlear stimulator (ICS) circuit. The circuit diagram of FIG. 1B shows only a portion of the ICS circuit which receives signal transmissions through the skin from the external transmitting coil 340 (FIG. 1A) and provides a rectified voltage which is supplied at node 30, supplying a voltage, Vp, and node 40, supplying a voltage, Vn. These supply voltages are used by additional processing circuitry and stimulation channels which are not shown in FIG. 1B. The portion of the ICS circuit shown has a coupling (implanted receiving) coil (L1) 10 and tuning capacitor (C1) 20. Rectifying diodes (D1) 50 and (D2) 60 rectify the transmitted signal received at coupling coil 10 and generate the voltages, Vp and Vn, at nodes 30 and 40, respectively. Capacitors 35 (C3) and 45 (C2) are rectifier filter capacitors which function to provide a D.C. voltage with low ripple at output nodes 30 and 40. A ground 160 is connected between these capacitors.

The detection circuit in FIG. 1B includes a detection resistor (R1) 80 and a detection capacitor (C4) 90. It can be seen that the detection resistor 80 is placed directly in the rectifying circuit. As such, the voltage detected at electrical node 70, signified in the schematic as "FT," is less (more negative) than the voltage, Vn, at node 40.

The rectification of the RF voltage acquired at coupling coil 10 produces current pulses through the diode 50. The time average of these pulses can be detected across the detection resistor 80 and the detection capacitor 90. The time constants for the detection resistor and the detection capacitor are chosen to be short enough to produce a data envelope which is representative of the ON/OFF data stream.

The voltage developed across the detection resistor 80 disadvantageously reduces the voltage, Vn, at node 40. The signal amplitude of FT, at node 70, is directly proportional to the rectified current. If the ICS processing circuit and stimulation channels are drawing low power, then the rectified current detected is small and may be difficult to process. The value of the detection resistor 80 used in the detection circuitry is a compromise between the desire to obtain a large output voltage when the rectification current is small and the desire to have a small output voltage when the current is large. In the former case, the output voltage must be large enough to be easily processed. In the latter case, when the rectified current is large, the output voltage is sufficiently large for processing, but power is being consumed by the detection resistor. In this detection circuit design, an additional diode (not shown) can be placed in parallel with the detection resistor to function as a diode clamp for limiting the maximum voltage developed across the detection resistor.

When the presently practiced detection design is used, constraints are placed on the circuitry design that can be attached to node 70 because the stimulation channels and processing electronics are operated from power supplied at nodes 30 and 40. To prevent reduction to the supply voltages, the detection circuit can only provide small detection signals FT at node 70, which restricts the range of operation of the detection circuit.

Figure 2:
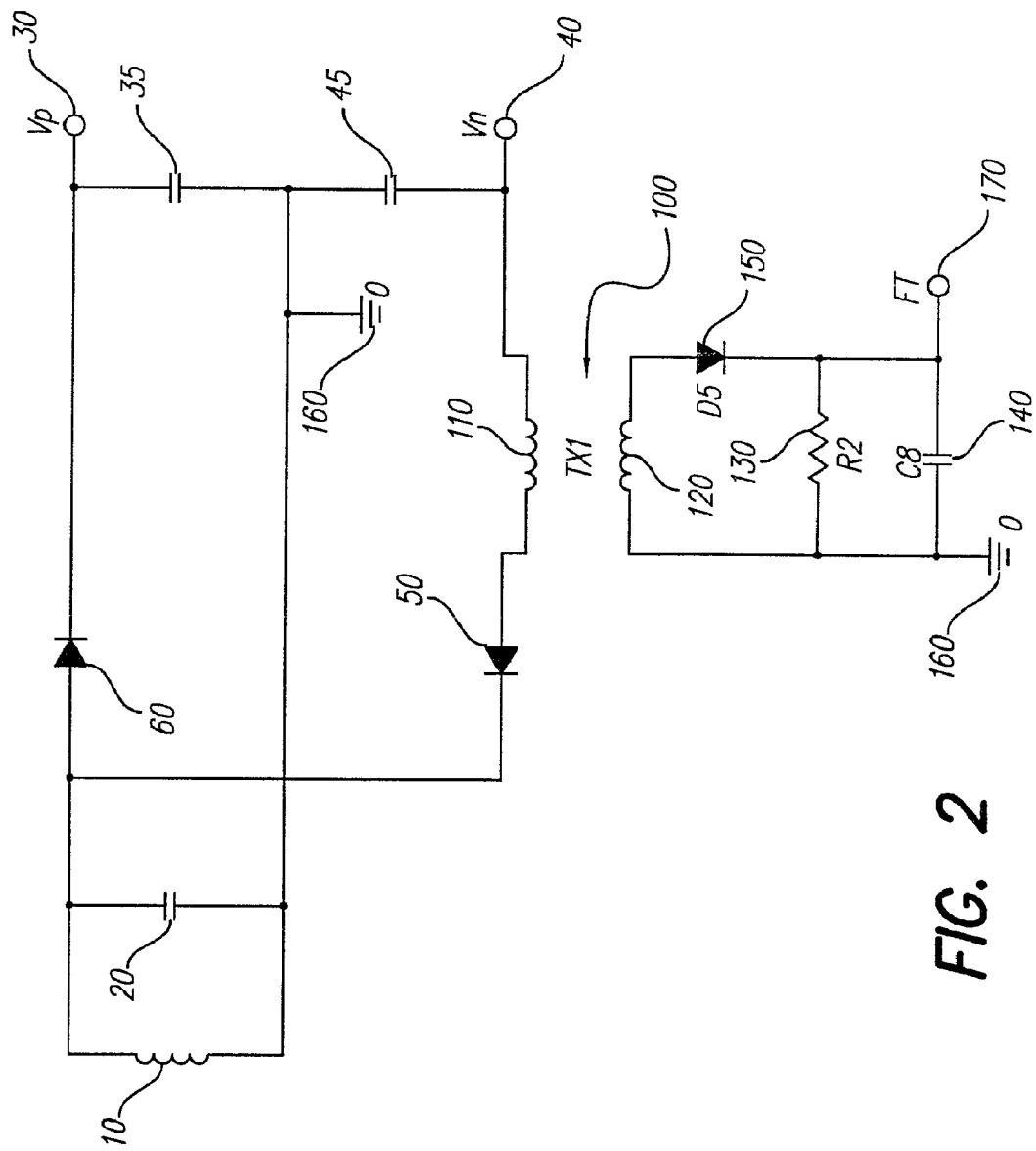
FIG. 2 shows a schematic diagram of the detection circuit, in accordance with the present invention, which detection circuit is coupled by a transformer to a rectification circuit which is part of an ICS.

FIG. 2 shows a schematic circuit diagram showing a portion of the ICS circuit for rectifying data signals from the external component and providing supply voltages at nodes 30 and 40. FIG. 2 also shows an exemplary detection circuit, in accordance with the present invention, which is used to detect the current data envelope in the rectifying circuit.

The detection circuit includes a transformer (TX1) 100. The secondary winding 120 of TX1 is connected to an isolated circuit having a resistor (R2) 130, a capacitor (C8) 140, and a diode (D5) 150 that are referenced to ground node 160. The primary winding 110 of TX1 can have one or a few turns, while the secondary winding 120 of TX1 can have many turns. The impedance of the primary winding is very small, so that the voltage drop across the primary winding is also very small.

Because the secondary winding is isolated from the primary winding, the output can be referenced to any convenient node for signal processing. The impedance transforming properties of current sensing coil 100 (TX1) allows a relatively large resistor 130 to be used in the isolated, envelope detector circuit. This enables a large output voltage to be developed across this resistor, which voltage obtained is larger than is possible with the conventional detection circuit provided in FIG. 1B.

The detector diode 150 can be a zero-bias Schottky diode which does not require a forward bias current in order to obtain maximum sensitivity and does not have any DC offset associated with a bias current. These characteristics simplify subsequent signal processing. Capacitor (C8) 140 resonates the secondary winding 120 of TX1, the combination of the capacitor-winding forming a single-tuned transformer network.

Figure 3:
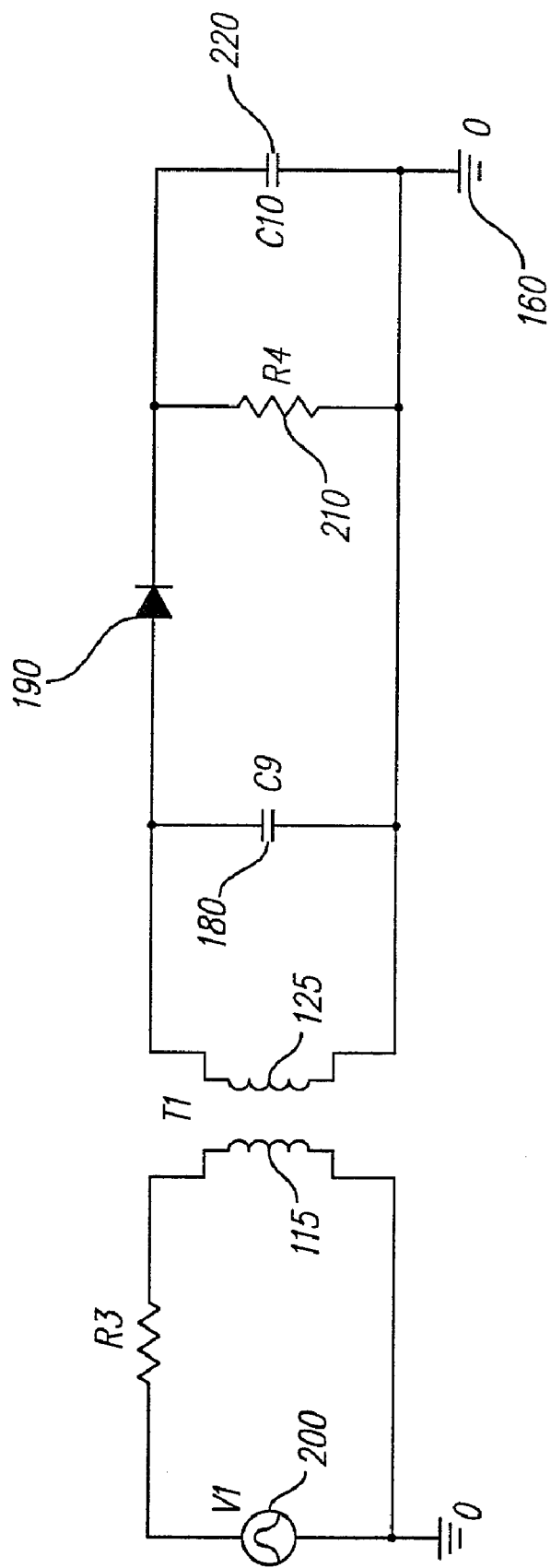
FIG. 3 shows a schematic circuit diagram of an experimental set-up to test the performance of the detection circuit of the present invention.

FIG. 3 shows a test circuit used to experimentally verify the operation of the detection circuit of the present invention, as exemplified in FIG. 2. A transformer, T1, was used, which had a small, powdered-iron toroid core 0.100 inches in diameter. The detection circuit of the present invention preferably use a primary winding having between 1 and 5 turns and a secondary winding preferably having between 15 to 25 turns. The coupling coefficient of T1 was 0.56. The coupling coefficient T1 should be at least 0.1 and typically between 0.5 and 0.7, using the detection circuit of the present invention. In the test circuit, the primary winding 115 had 3 turns, and the secondary winding 125 had 23 turns. Using this information and the measured primary and secondary inductance, the circuit was constructed so that capacitor 180 would resonate the secondary inductance. This capacitor 180 is an additional capacitor not shown in FIG. 2. This additional capacitor further tunes the isolated circuit to enable it to operate effectively in a narrower range. A zero-bias, Schottky detector diode 190 was used in the detection circuit, in addition to the usual detection resistor 200 and detection capacitor 210. A pulse generator (V1) 200 with a gated output was used to generate current pulses at 49 MHz pulse bursts with a 1.11 MHz repetition rate.

Figure 4:
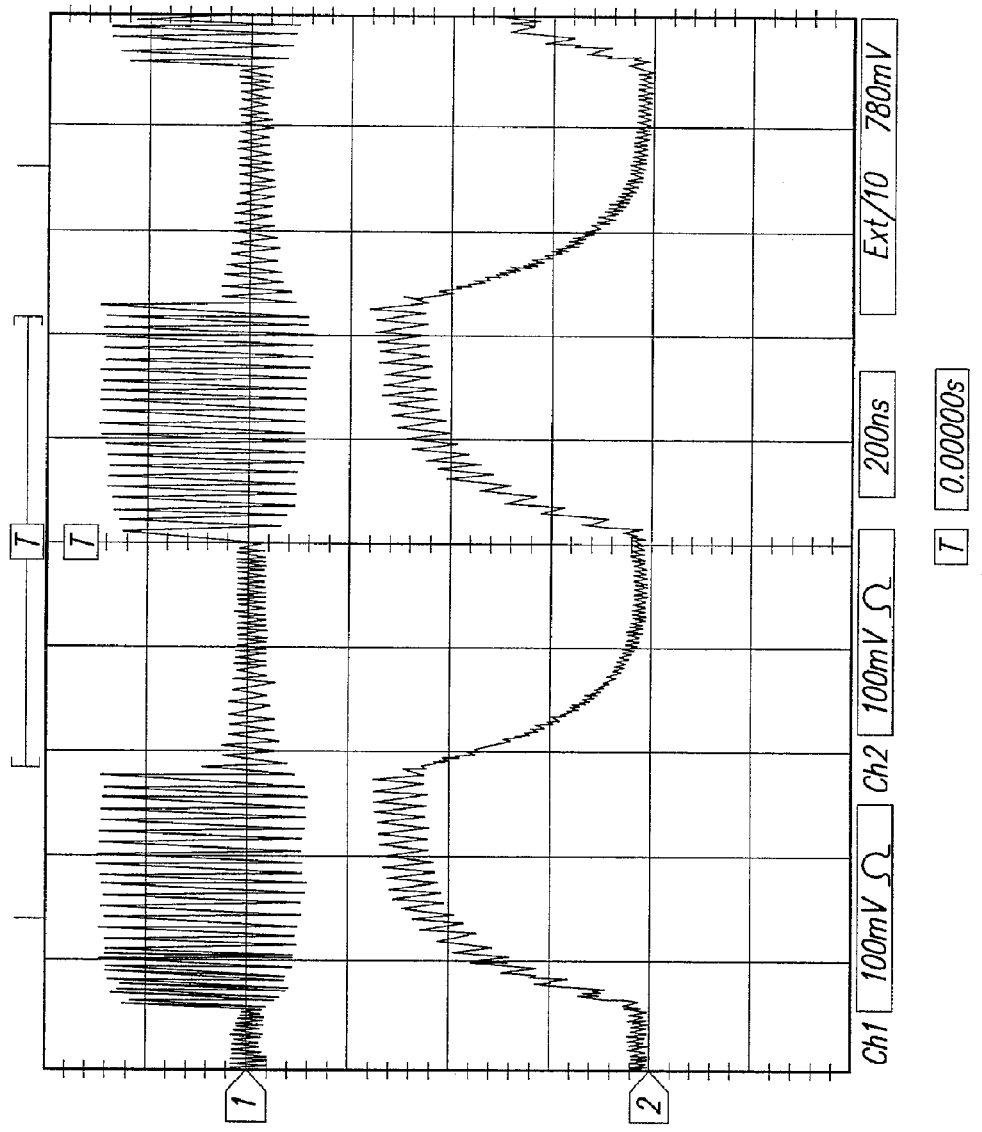
FIG. 4 shows waveforms resulting from the experimental test set-up depicted in FIG. 3.

FIG. 4 shows the waveforms of the generator voltage, V1 (upper trace), and the resulting detector output voltage (lower trace), which were monitored with high-bandwidth FET probes and displayed on an oscilloscope. The input voltage was pulsed to an amplitude of 100 mV corresponding to 2 mA pulses. The detected voltage peaked at 240 mV. The rise/fall time was controlled by choosing the time constant of the detection circuit resistor 200 and capacitor 210.

The power dissipated in the load resistor of the detection circuit of the present invention was approximately 2.95 µW. In comparison, an ICS detection circuit, using a 750 ohms series resistor in conformity with present, conventional practice, dissipated about 367 µW for the same current pulse output format. Thus, the power savings with the detection circuitry of the present invention were substantial.

In addition to obtaining power savings, the detection circuit of the present invention is advantageous because the detected voltage can be scaled by changing the coupling coefficients and the values for resistor 200 and capacitor 210, without compromising the output supply voltages, Vp and Vn. This enhances the flexibility and usability of the detection circuit.

It will be appreciated that there are a number of modifications which can be made to the present invention. The present invention provides an isolated detection circuit which uses a transformer, having a primary coil in the sensed ICS circuit and a secondary coil in the isolated detection circuit. Various circuit means may be employed in the isolated detection circuit. The types and numbers of circuit parts, including diodes, resistors and capacitors may be used to form the isolated detection circuit which can process the induced current in the detection circuit. A particular circuit means for the detection circuit includes the use of a Hall current sensing device. Although a Hall sensor may require a specific amplifier circuit, it has the advantage of being able to directly sense DC, as well as AC currents.

While the invention herein disclosed has been described by means of specific embodiments and applications thereof, numerous modifications and variations could be made thereto by those skilled in the art without departing from the scope of the invention set forth in the claims.

What is claimed is:

1. Circuitry for an implantable medical device having a housing, comprising:
   a rectifying circuit within the housing connected to a first coil, wherein the first coil receives digital data from a source external to the implantable medical device, wherein the rectifying circuit outputs at least one DC voltage;
   a second coil within the housing for receiving a current in the rectifying circuit indicative of the reception of digital data at the first coil; and
   a third coil within the housing forming a transformer with the second coil;
   a processing circuit within the housing coupled to the third coil, the processing circuit for producing a signal indicative of the reception of the digital data.

2. The circuitry of claim 1, wherein the at least one DC voltage comprises at least one power supply voltage for the implantable medical device.

3. The circuitry of claim 2, wherein the implantable medical device comprises an electrical neurostimulator device with at least one stimulating electrode, and wherein the at least one power supply voltage provides power to the at least one stimulating electrode.

4. The circuitry of claim 1, wherein the processing circuit comprises:
   a diode connected in series with the third coil;
   a capacitor connected in parallel with the series-connected diode and third coil; and
   a resistor connected in parallel with the capacitor.

5. The circuitry of claim 4, wherein the diode is a zero-bias Schottky diode.

6. The circuitry of claim 1, wherein the processing circuit includes a Hall sensor.

7. The circuitry of claim 1, wherein a coupling coefficient of the transformer comprised of the second coil and the third coil is at least 0.1.

8. An implantable medical device having a housing, comprising:
- a first coil for receiving digital data from a source external to the implantable medical device;
- a rectifying circuit within the housing connected to the first coil, wherein the rectifying circuit outputs at least one DC voltage;
- a detection circuit within the housing for detecting the receipt of digital data at the first coil, comprising:
  - a second coil for receiving a current in the rectifying circuit indicative of the reception of the digital data at the first coil;
  - a third coil forming a transformer with the second coil; and
    - a processing circuit coupled to the third coil, the processing circuit for producing a signal indicative of the reception of the digital data.

9. The implantable medical device of claim 8, wherein the at least one DC voltage comprises at least one power supply voltage for the implantable medical device.

10. The implantable medical device of claim 9, wherein the implantable medical device comprises an electrical neurostimulator device with at least one stimulating electrode, and wherein the at least one power supply voltage provides power to the at least one stimulating electrode.

11. The implantable medical device of claim 8, wherein the processing circuit comprises:
- a diode connected in series with the third coil;
- a capacitor connected in parallel with the series-connected diode and third coil; and
- a resistor connected in parallel with the capacitor.

12. The implantable medical device of claim 11, wherein the diode is a zero-bias Schottky diode.

13. The implantable medical device of claim 8, wherein the processing circuit includes a Hall sensor.

14. The implantable medical device of claim 8, wherein the coupling coefficient of the transformer comprised of the second coil and the third winding is at least 0.1.

* * * * *

UNITED STATES PATENT AND TRADEMARK OFFICE
CERTIFICATE OF CORRECTION

| | | |
|---|---|---|
| PATENT NO. | : 7,623,929 B1 | Page 1 of 1 |
| APPLICATION NO. | : 10/651650 | |
| DATED | : November 24, 2009 | |
| INVENTOR(S) | : Griffith | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 721 days.

Signed and Sealed this

Eleventh Day of January, 2011

David J. Kappos
*Director of the United States Patent and Trademark Office*